(12) United States Patent
Ji et al.

(10) Patent No.: US 11,344,242 B2
(45) Date of Patent: May 31, 2022

(54) VITAL-SIGN DATA STATISTICS SYSTEM AND PATIENT MONITOR

(71) Applicant: Shenzhen Mindray Bio-Medical Electronics Co., Ltd., Shenzhen (CN)

(72) Inventors: Baimiao Ji, Shenzhen (CN); Jianhui Zhang, Shenzhen (CN); Ming Yi Tan, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 366 days.

(21) Appl. No.: 16/293,336

(22) Filed: Mar. 5, 2019

(65) Prior Publication Data

US 2019/0216349 A1 Jul. 18, 2019

Related U.S. Application Data

(63) Continuation of application No. PCT/CN2016/098136, filed on Sep. 5, 2016.

(51) Int. Cl.
*A61B 5/316* (2021.01)
*G16H 40/63* (2018.01)
(Continued)

(52) U.S. Cl.
CPC ............... *A61B 5/316* (2021.01); *A61B 5/00* (2013.01); *A61B 5/002* (2013.01); *A61B 5/0205* (2013.01);
(Continued)

(58) Field of Classification Search
CPC ........... A61B 5/316; A61B 5/366; A61B 5/00; A61B 5/002; A61B 5/0205; A61B 5/02055; A61B 5/7235; A61B 5/7285; A61B 5/352; A61B 5/361; A61B 5/0006; A61B 5/0024; A61B 5/7282; A61B 5/742; A61B 5/7475; G16H 40/63
See application file for complete search history.

(56) References Cited

U.S. PATENT DOCUMENTS 6,188,407 B1 * 2/2001 Smith ................ G16H 40/67
715/841
7,001,338 B2 2/2006 Hayek et al.
(Continued)

FOREIGN PATENT DOCUMENTS

CN 1395214 A 2/2003
CN 101779950 A 7/2010
(Continued)

*Primary Examiner* — Gary Jackson
*Assistant Examiner* — Sebastian X Lukjan
(74) *Attorney, Agent, or Firm* — Kory D. Christensen (57) ABSTRACT

Provided are a patient monitor and vital-sign data statistics system, having vital-sign data statistics functionality. The patient monitor includes a signal acquisition module, a data processing module, and a display module. The data processing module processes the vital-sign signal acquired by the signal acquisition module and generates physiological parameters. If request information requesting to display a vital-sign data statistics result is received, then the data processing module statistically classifies the vital-sign data within a preset time range according to set type and a statistical item of each type, and displays the data by means of the display module.

14 Claims, 5 Drawing Sheets

(51) Int. Cl.
  *A61B 5/00*     (2006.01)
  *A61B 5/0205*   (2006.01)
  *A61B 5/366*    (2021.01)
  *A61B 5/352*    (2021.01)
  *A61B 5/361*    (2021.01)

(52) U.S. Cl.
  CPC .......... *A61B 5/02055* (2013.01); *A61B 5/366* (2021.01); *A61B 5/7235* (2013.01); *A61B 5/7285* (2013.01); *G16H 40/63* (2018.01); *A61B 5/0006* (2013.01); *A61B 5/0024* (2013.01); *A61B 5/352* (2021.01); *A61B 5/361* (2021.01); *A61B 5/7282* (2013.01); *A61B 5/742* (2013.01); *A61B 5/7475* (2013.01)

(56) References Cited

U.S. PATENT DOCUMENTS

| | | | |
|---|---|---|---|
| 8,521,267 B1* | 8/2013 | Jalali | A61B 5/0031 600/516 |
| 2006/0167364 A1 | 7/2006 | Houben | |
| 2009/0149717 A1 | 6/2009 | Brauer et al. | |
| 2011/0213620 A1 | 9/2011 | Dziubinski | |
| 2014/0107509 A1* | 4/2014 | Banet | A61B 5/0022 600/515 |
| 2014/0275819 A1* | 9/2014 | Kassem | A61B 5/14551 600/301 |
| 2014/0285490 A1* | 9/2014 | Gilger | G06F 3/04817 345/440 |
| 2016/0058359 A1 | 3/2016 | Osorio | |
| 2016/0345854 A1* | 12/2016 | Bardy | A61B 5/02405 |

FOREIGN PATENT DOCUMENTS

| | | | |
|---|---|---|---|
| CN | 102281816 A | 12/2011 | |
| CN | 102697492 A | 10/2012 | |
| CN | 102743157 A | 10/2012 | |
| CN | 102908135 A | 2/2013 | |
| CN | 102743157 B | 1/2015 | |
| CN | 104887189 A | 9/2015 | |
| CN | 105147277 A | 12/2015 | |
| JP | 2010233953 A | 10/2010 | |
| WO | WO-2012158720 A1 * | 11/2012 | ............ A61B 5/339 |
| WO | WO 2015/087244 A1 | 6/2015 | |

* cited by examiner

VITAL-SIGN DATA STATISTICS SYSTEM AND PATIENT MONITOR

CROSS-REFERENCE TO RELATED APPLICATIONS

This application is a continuation of Patent Cooperation Treaty (PCT) App. No. PCT/CN2016/098136, filed Sep. 5, 2016, for "VITAL-SIGN DATA STATISTICS SYSTEM AND MONITOR," which is incorporated herein by reference.

TECHNICAL FIELD

The disclosure relates to a patient monitoring, and in particular to a vital-sign data statistics system and patient monitor.

BACKGROUND ART

For clinical critical or sub-critical hospitalized patients, especially CCU and ICU patients, 24-hour monitoring is required. A patient monitor can be used to analyze and display various physiological and/or psychological parameters measured by one or more sensors connected to the patient. These parameters may be displayed in the form of waveforms or numerical values, where the waveforms can display parameter values within a certain period of time (e.g. 1 hour) and the numerical values can display current monitored values. Therefore, physicians can use the patient monitor to monitor the physical condition of the patient and assess the physical condition of the patient according to the measured parameters.

Physicians, when making ward rounds, need to know not only the current physiological parameters of the patients, but also the overall condition of the patients for 24 hours or more and some special data that are of guiding significance to medicine. However, existing patient monitors do not have this function, so that it is necessary for the physicians to manually retrieve these data for manual statistics and analysis, which not only causes the physicians to spend much time and energy collating and analyzing the data, but also is prone to errors in the statistical process, causing the physicians to make wrong judgments.

BRIEF SUMMARY

According to one aspect, there is provided a vital-sign data statistics system including a request receiving unit for receiving request information for requesting display of statistical results of vital sign data; a first acquisition unit for acquiring a time range of statistical data based on the request information; a statistical unit for applying statistics by category to the vital sign data within the time range according to set categories and statistical items of each of the set categories; and a display unit for processing the statistical results of each category into visual data and displaying the visual data by category in a statistical result display area which is at least a partial area of a display interface.

According to another aspect, there is provided a patient monitor including a signal collection module for collecting vital sign signals of a patient from the body of the patient; a data processing module, which is connected to the signal collection module and configured to process the vital sign signals and generating physiological parameters for reflecting condition of the patient. The data processing module may be further configured to receive request information for requesting display of statistical results of vital sign data, acquire a time range of statistical data based on the request information, apply statistics by category to the vital sign data within the time range according to set categories and statistical items of each of the set categories, and process the statistical results of each category into visual data capable of being displayed in a statistical result display area which is at least a partial area of a display interface. The patient monitor may also include a display module, which is connected to the data processing module and configured to display the data output by the data processing module.

The vital sign data can be automatically and statistically analyzed by the patient monitor according to the preset categories, and the statistical analysis results can be intuitively presented to the physician on a display screen. This adds additional functions to the patient monitor, so that the patient monitor can not only assist the physicians to quickly learn about the overall condition of the patient for a relatively long time, but also saves the physician's time and energy and plays a positive role in relieving the strain on medical resources.

DETAILED DESCRIPTION

Specific embodiments are discussed in detail below in conjunction with the accompanying drawings, where similar elements in various embodiments are designated by associated similar reference numerals. In the following embodiments, many details are described for the purpose of facilitating better understanding of the present application. However, it would be appreciated by those skilled in the art that some features may be omitted or may be substituted by other elements, materials and methods in different situations. In some cases, well-known operations are not displayed or described in detail in order to avoid obscuring more relevant aspects.

In addition, the characteristics, operations or features described hereafter may be combined in any appropriate manner to form various embodiments. Moreover, the steps or actions in the method description may also be changed or adjusted in sequence in a way that would be understood by those skilled in the art. Therefore, the various sequences in the description and drawings are only for the purpose of clearly describing a certain embodiment and are not meant to imply a necessary sequence that must be followed, unless otherwise specified.

Embodiment I

Figure 1:
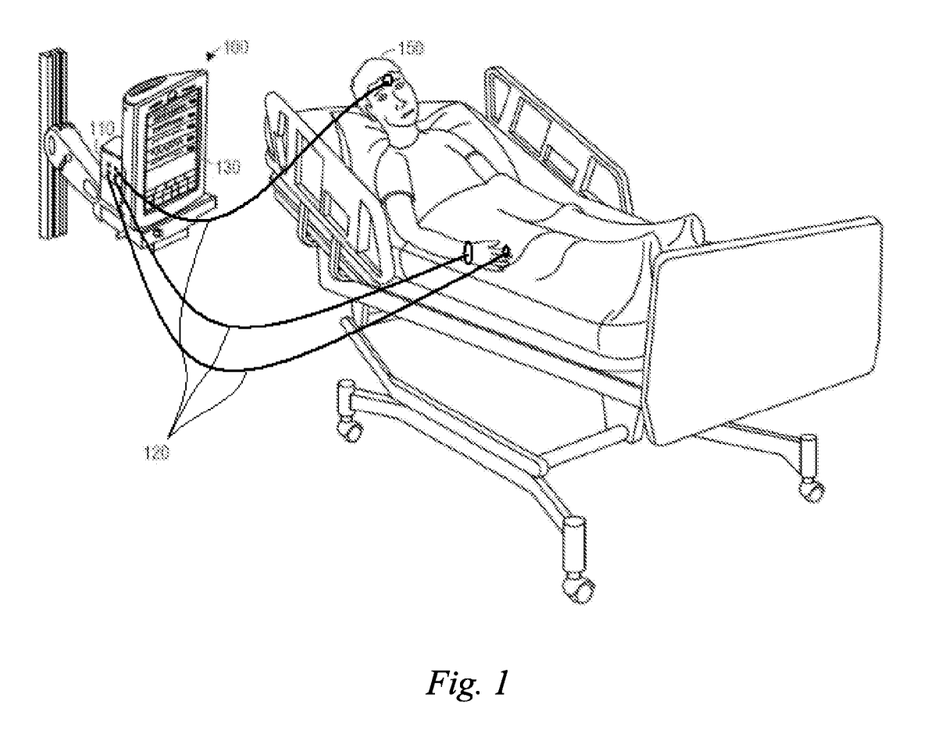
FIG. 1 is a schematic structural diagram of a patient monitor.

Referring to FIG. 1, this embodiment provides a patient monitor 100 for monitoring a patient 150. The patient monitor 100 includes a data processing module 110, a signal collection module 120, and a display module 130.

One end of the signal collection module 120 is used for making contact with the body of a patient from which vital sign signals of the patient are collected, such as pulse signals caused by heart beats, body temperature signals, blood absorption signals for light of a specific wave band, electrocardiogram (ECG) signals, electroencephalogram (EEG) signals, etc. The other end of the signal collection module 120 is connected to the data processing module 110 via, for example, an interface to input the vital sign signals to the data processing module 110.

The data processing module 110 is connected to the signal collection module 120 and the display module 130, respectively, and receives the vital sign signals, processes the vital sign signals, generates physiological parameters for reflecting the condition of the patient, and processes the physiological parameters into visual data. The visual data are then sent to the display module 130, such that the display module 130 displays the visual data on a display interface. The physiological parameters may include, for example, blood pressure, blood oxygen saturation, heart rate, body temperature, electrocardiogram, etc.

The display module 130 includes a display screen providing the display interface, which display screen may be of a touch or non-touch variety.

In general, a patient monitor displays standard physiological parameters in a graphical or numerical manner on its display screen. In this embodiment, the data processing module 110 further includes a vital-sign data statistics system. When a user (such as a physician) needs to view the summary and statistical analysis results of a patient for a long period of time, the vital-sign data statistics system performs statistical analysis on the designated vital sign data within a set time range according to the physician's request and displays the statistical analysis results on the display screen.

For example, a window displaying statistical analysis results can pop up, which can be part of the display interface or the entire display interface. For example, the window displaying statistical analysis results covers the display window of standard physiological parameters. The window of statistical analysis results can be closed by the user through operation, or the window of statistical analysis results can be automatically closed after a set time without operation, and the display window of standard physiological parameters can be re-displayed.

The designated vital sign data may be ECG data, pulse data, blood oxygen saturation data, EEG data, etc. The ECG data refer to parameters calculated or statistically derived according to electrocardiogram signals. The pulse data refer to parameters calculated or statistically derived according to pulse signals. The blood oxygen saturation data refer to parameters calculated or statistically derived according to blood oxygen saturation signals. The EEG data are parameters calculated or statistically derived according to EEG signals. Various vital sign data monitored are stored in memory, each including a numerical value and a monitoring time.

The following describes one embodiment of the present disclosure by taking statistical analysis of ECG data as an example.

In order to carry out statistical analysis on the ECG data, statistical categories of ECG data and statistical items of each category are determined in advance according to the items that physicians pay more attention to. For example, a category table is maintained in advance in the system, in which the statistical categories of the ECG data and the statistical items of each category are recorded.

In this embodiment, the statistics of ECG data are divided into four categories, including heart rate, ST, QT/QTc and arrhythmia events. In other embodiments, more categories or less categories of ECG data can be counted, and the statistical categories can include at least one of heart rate, ST, QT/QTc and arrhythmia events, or can exclude any one of heart rate, ST, QT/QTc and arrhythmia events.

For each category, statistical items thereof are also specified. For example, for heart rate, the statistical items thereof include the total number of heart beats, average heart rate, the fastest heart rate and its occurrence time, and the slowest heart rate and its occurrence time in the current statistical period. For ST, the statistical items thereof include the ST elevation and depression frequency of each ECG lead in the current statistical period, the maximum ST elevation and depression values of each ECG lead and their occurrence time, etc. For QT/QTc, the statistical items thereof include the maximum QT value, minimum QT value and average QT value as well as the maximum QTc value, minimum QTc value and average QTc value, etc. in the current statistical period. For arrhythmia events, the statistical items thereof include all arrhythmia events occurring in the current statistical period and the total number of occurrences of each type of arrhythmia events, etc. Of course, those skilled in the art will understand that in other embodiments, statistical items different from those in this embodiment can also be used, or statistical categories and/or statistical items can be designed to be selected by the user.

Figure 2:
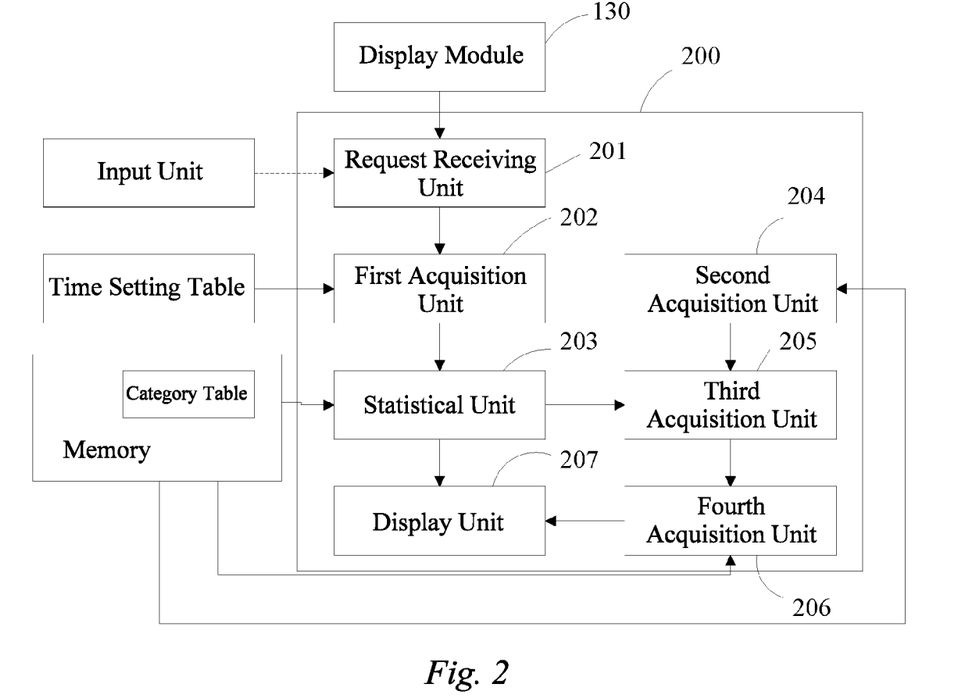
FIG. 2 is a schematic structural diagram of a vital-sign data statistics system.

Referring to FIG. 2, a vital-sign data statistics system 200 includes a request receiving unit 201, a first acquisition unit 202, a statistical unit 203, a second acquisition unit 204, a third acquisition unit 205, a fourth acquisition unit 206 and a display unit 207.

The request receiving unit 201 is configured to receive request information for requesting display of statistical results of vital sign data. In one embodiment, the request information is generated based on the selection operation of the user on the display interface, so the request receiving unit 201 is connected to the display module 130, as shown by a solid line in FIG. 2.

In another embodiment, the request information is generated based on the switching by the user of the state of an input unit provided on the patient monitor, so the request receiving unit 201 is connected to the input unit, which may be a button, a knob or slide switch having different settings, etc., as shown by a dashed line in FIG. 2. In this embodiment, the request information is used to request display of the statistical results of the ECG data.

The first acquisition unit 202 is connected to the request receiving unit 201 and is configured to acquire a time range of the statistical data based on the request information and output the acquired time range to the statistical unit 203. In one embodiment, the time range may be a time period preset in the system, such as the latest 24 hours, or the latest 12 hours, etc. The first acquisition unit 202 may acquire the time range of statistical data from a time setting table, as shown in FIG. 2.

In another embodiment, after receiving the request information, the first acquisition unit 202 may pop up a dialog window asking the user to input a time range of statistical data, after which the first acquisition unit 202 outputs the time range to the statistical unit 203.

The statistical unit 203 is configured to perform statistical analysis by category on the vital sign data within the time range according to set categories and statistical items of each of the set categories. In this embodiment, the statistical unit 203 is respectively connected to the first acquisition unit 202 and the memory, receives the time range output by the first acquisition unit 202, and acquires the statistical categories of ECG data and statistical items of each category from the category table stored in the memory. In this embodiment, statistics by category are applied to ECG data such as heart rate, ST, QT/QTc and arrhythmia events. Therefore, ECG data of these categories within this time range are read from the memory for statistical analysis, in which various statistical items of heart rate, ST, QT/QTc and arrhythmia events are obtained through statistics and analysis, and the statistical analysis results are sent to the display unit 207.

The second acquisition unit 204 is configured to acquire special statistical items set for each category. Special statistical items are usually statistical items of greater importance, which play a role, to some extent, in guiding the physicians to assess the patient's condition. Special statistical items or no special statistical items may be specified for a certain type of ECG data. In one embodiment, the special statistical items may also be specified in the category table, so the second acquisition unit 204 is also connected to the memory to read the special statistical items of each category from the category table stored in the memory.

For example, the special statistical items for heart rate are the fastest heart rate and the slowest heart rate, ST has no special statistical items, the special statistical items for QT/QTc are the maximum QT value, the minimum QT value, the maximum QTc value and the minimum QTc value, and the special statistical items for arrhythmia events are one or some arrhythmia events, such as cardiac arrest and single premature ventricular contraction. Those skilled in the art should understand that the provisions for special statistical items can be set according to different requirements. In practical application, default special statistical items of the system can be used, and the physicians can also be allowed to modify the special statistical items. The second acquisition unit 204 is connected to the third acquisition unit 205, and the second acquisition unit 204 outputs the special statistical items read from the memory to the third acquisition unit 205.

The third acquisition unit 205 is also connected to the statistical unit 203, and is used for acquiring the statistical results of the special statistical items in the statistical contents of each category. For example, for the special statistical item of fastest heart rate, the third acquisition unit 205 acquires the fastest heart rate of 144 bpm from the statistical results of the heart rate, which occurs at 09:01:00; for the special statistical item of slowest heart rate, the third acquisition unit 205 acquires the slowest heart rate of 46 bpm from the statistical results of the heart rate, which occurs at 04:01:00; and for the special statistical item of cardiac arrest, the number of cardiac arrests acquired by the third acquisition unit 205 from the statistical results of arrhythmia is 53. The third acquisition unit 205 is connected to the fourth acquisition unit 206 and transmits the obtained statistical results of the special statistical items to the fourth acquisition unit 206.

The fourth acquisition unit 206 is connected to the memory and the display unit 207 respectively, extracts waveform data including a predetermined period of time (for example, 20 seconds or 30 seconds) around the statistical result of the special statistical item from the ECG data within a preset time range, and sends the waveform data to the display unit 207 as typical waveform data of the special statistical item.

The display unit 207 is configured to process the received data into visual data to be displayed on the display interface. In this embodiment, the display unit 207 is connected to the statistical unit 203 and the fourth acquisition unit 206, respectively. In one embodiment, the display unit 207 processes the statistical analysis results of each category of ECG data sent from the statistical unit 203 into visual data, and displays same by category in a statistical result display area, which is at least a partial area of a display interface. In another aspect, the display unit 207 processes the transmitted typical waveform data into visual data to be respectively displayed in a waveform display area, which is at least a partial area of the display interface.

Figure 3:
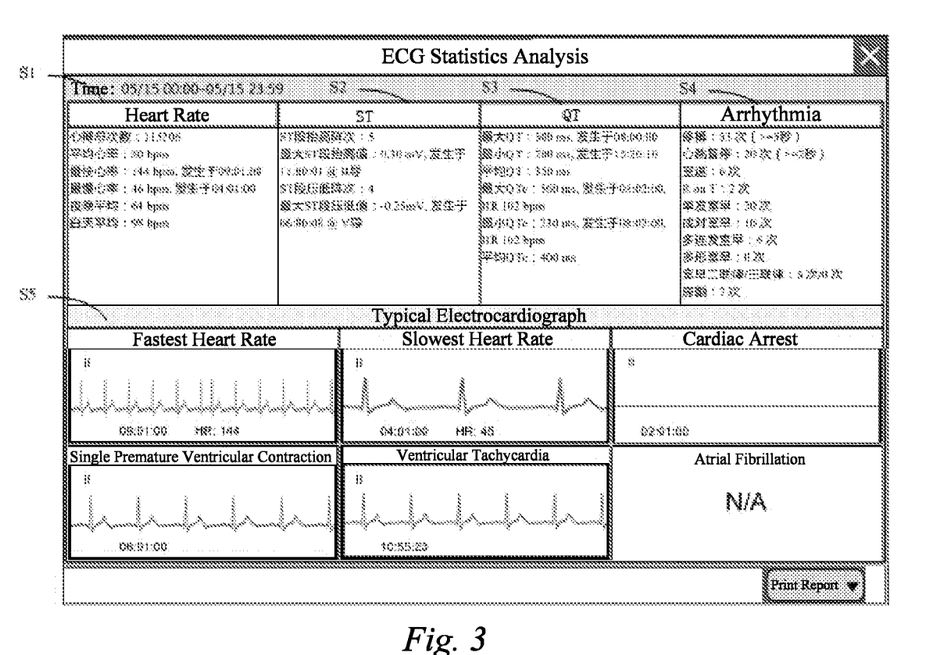
FIG. 3 is a display interface of statistical results of electrocardiogram (ECG) data.

In this embodiment, the statistical result display area and the waveform display area are two areas arranged vertically side by side on the display interface, as shown in FIG. 3. The statistical result display area is divided into a plurality of sub-areas, each sub-area displaying the statistical results of a category of ECG data. For example, in FIG. 3, the statistical result display area is divided into a heart rate statistics area S1, a ST statistics area S2, a QT/QTc statistics area S3, and an arrhythmia statistics area S4. The waveform display area S5 is also divided into several sub-areas, and each sub-area displays typical waveform data of a special statistical item. In other embodiments, the statistical result display area and the waveform display area may also be two areas arranged horizontally side by side on the display interface.

In this embodiment, after various vital sign data are classified for statistics, the typical waveform of the special statistical item can also be displayed according to the preset special statistical item, so that physicians can check the waveform conditions before and after the special statistical item occurs and provide a visual basis for the physicians to make comprehensive judgment.

Those skilled in the art should understand that in other embodiments, the vital-sign data statistics system 200 may not include the second acquisition unit 204, the third acquisition unit 205, and the fourth acquisition unit 206, in which case the display interface will not display the typical waveform data.

Embodiment II

Figure 4:
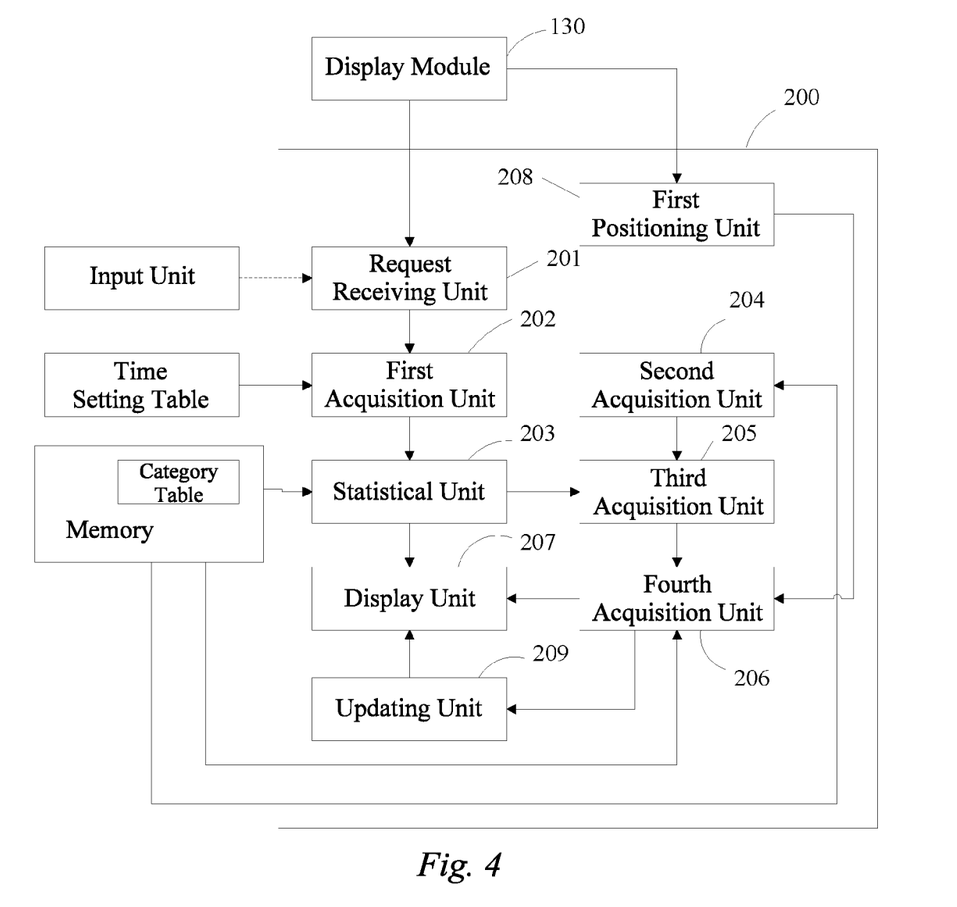
FIG. 4 is a schematic structural diagram of a vital-sign data statistics system.

This embodiment adds a typical waveform data setting function on the basis of embodiment I. As shown in FIG. 4, the vital-sign data statistics system 200 further includes a first positioning unit 208 and an updating unit 209.

The first positioning unit 208 is connected to the display module 130 and is used for capturing a user's selection operation in the waveform display area. The selection operation may be a click operation after the user controls and moves a cursor to a predetermined position. When the display module 130 includes a touch screen, the selection operation may also be a touch operation of the user at the predetermined position. After capturing the user's selection operation in the waveform display area, the first positioning unit 208 determines the special statistical item corresponding to the area selected by the user according to the position coordinates of the selection operation. The first positioning unit 208 is also connected to the fourth acquisition unit 206 and sends the special statistical item corresponding to the area selected by the user to the fourth acquisition unit 206.

Figure 5:
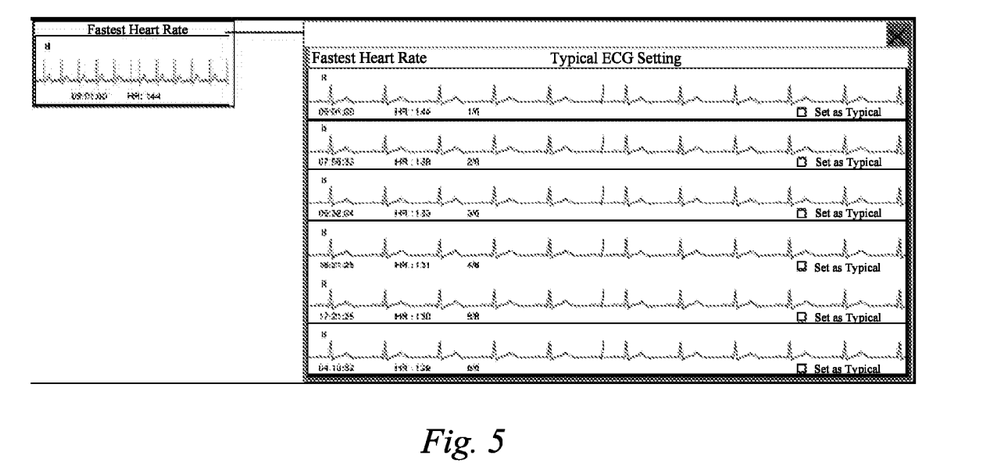
FIG. 5 is a schematic diagram of a typical waveform selection.

The fourth acquisition unit 206 retrieves at least one relevant datum related to the statistical results of the special statistical item from the vital sign data within the preset time range, then extracts at least one group of waveform data including a predetermined period of time around the relevant datum, and takes the at least one group of waveform data as alternative waveform data of the special statistical item and sends it to the display unit 207. The display unit 207 processes the typical waveform data and the alternative waveform data of the special statistical item into visual data to be displayed in rows in a pop-up selection window and allows the user to select between the typical waveform data and the alternative waveform data. The relevant datum may be data close to the statistical results of the special statistical item, for example, the special statistical item is the fastest/slowest heart rate, and the data close to the fastest/slowest heart rate is the second-fastest/second-slowest heart rate. A plurality of typical ECG waveforms may be accordingly selected in this order for the user to select, as shown in FIG. 5.

The update unit 209 is connected to the fourth acquisition unit 206 and the display unit 207, respectively, and is configured to update the typical waveform data initially displayed of the special statistical item to the typical waveform data selected by the user after receiving the user's selection between a plurality of typical ECG waveforms.

This embodiment can allow the user to manually select a non-disturbed ECG waveform as a typical waveform. When the user has questions about the typical waveform of the special statistic item, he or she can touch or click on the area where the typical waveform of the special statistical item is located, so that the system will automatically select a plurality of corresponding ECG waveforms according to the user's requirements for the user to select, and set the waveform selected by the user as the typical ECG waveform to prevent one of the typical waveforms from being a false aberration caused by interference of electrocardiogram signals.

Embodiment III

This embodiment adds the function of displaying holographic waveforms on the basis of embodiments I and II. The vital-sign data statistics system further includes a second positioning unit for capturing the selection operation of the user in the statistical result display area and determining the statistical item selected by the user according to the position coordinates of the selection operation. The display unit pops up a holographic waveform display window of the vital sign data based on the selection operation and processes the waveform related to the statistical item selected by the user to be displayed in the current window of the holographic waveform display window.

Figure 6:
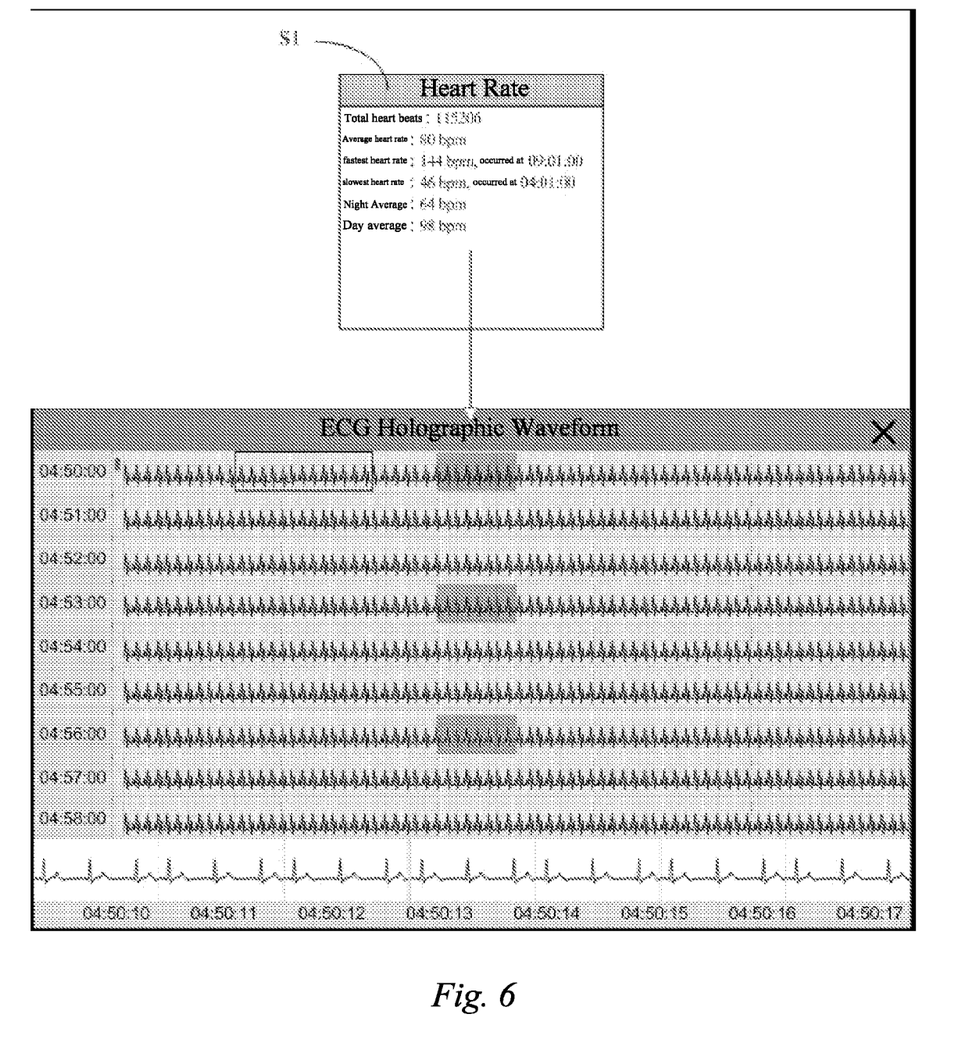
FIG. 6 is a schematic diagram of ECG holographic waveforms.

As shown in FIG. 6, when the user touches or clicks on the heart rate statistics area, the system pops up a holographic waveform display window. The so-called holographic waveform refers to the waveform including the waveform data of the entire statistical time range, which cannot be displayed in a single two-dimensional graph due to the long time and therefore are displayed in several two-dimensional graphs arranged vertically side by side by dividing the time period. For example, the waveform data of the first minute is displayed in the first two-dimensional graph, the waveform data of the second minute is displayed in the second two-dimensional graph, and so on, until all the waveform data of the entire statistical time range are displayed. The user can display preceding and succeeding waveforms through a scroll bar. Displaying holographic waveforms enables the physicians to conveniently view all ECG waveforms of the patients.

In one embodiment, in order to make it convenient for the physician to observe the waveform of the special statistical item, the waveform of an occurrence time of the special statistical item or the typical waveform of the special statistical item corresponding to the area selected by the user is displayed in the current window of the holographic waveform display window, so as to prevent the physicians from searching around. More preferably, the typical ECG waveform of a special statistical item is marked on the holographic waveform, and the typical ECG waveform is enlarged and displayed in a lower area of the holographic waveform display window, so as to facilitate observation by the physicians. As shown in FIG. 6, when the user clicks on the heart rate statistics area S1, a window is popped up displaying the electrocardiogram (ECG) holographic waveform, a one-minute ECG waveform including the occurrence time of the fastest heart rate of the special statistical item in the first row of the window, with the typical ECG waveform of 7 seconds of the fastest heart rate marked with a rectangular frame on the one-minute ECG waveform, and an enlarged view of the typical ECG waveform is displayed in the lower area of the window.

Each of the above units may be formed as a separate module or integrated in the data processing module, the display unit may also be a part of the display module.

Embodiment IV

Figure 7:
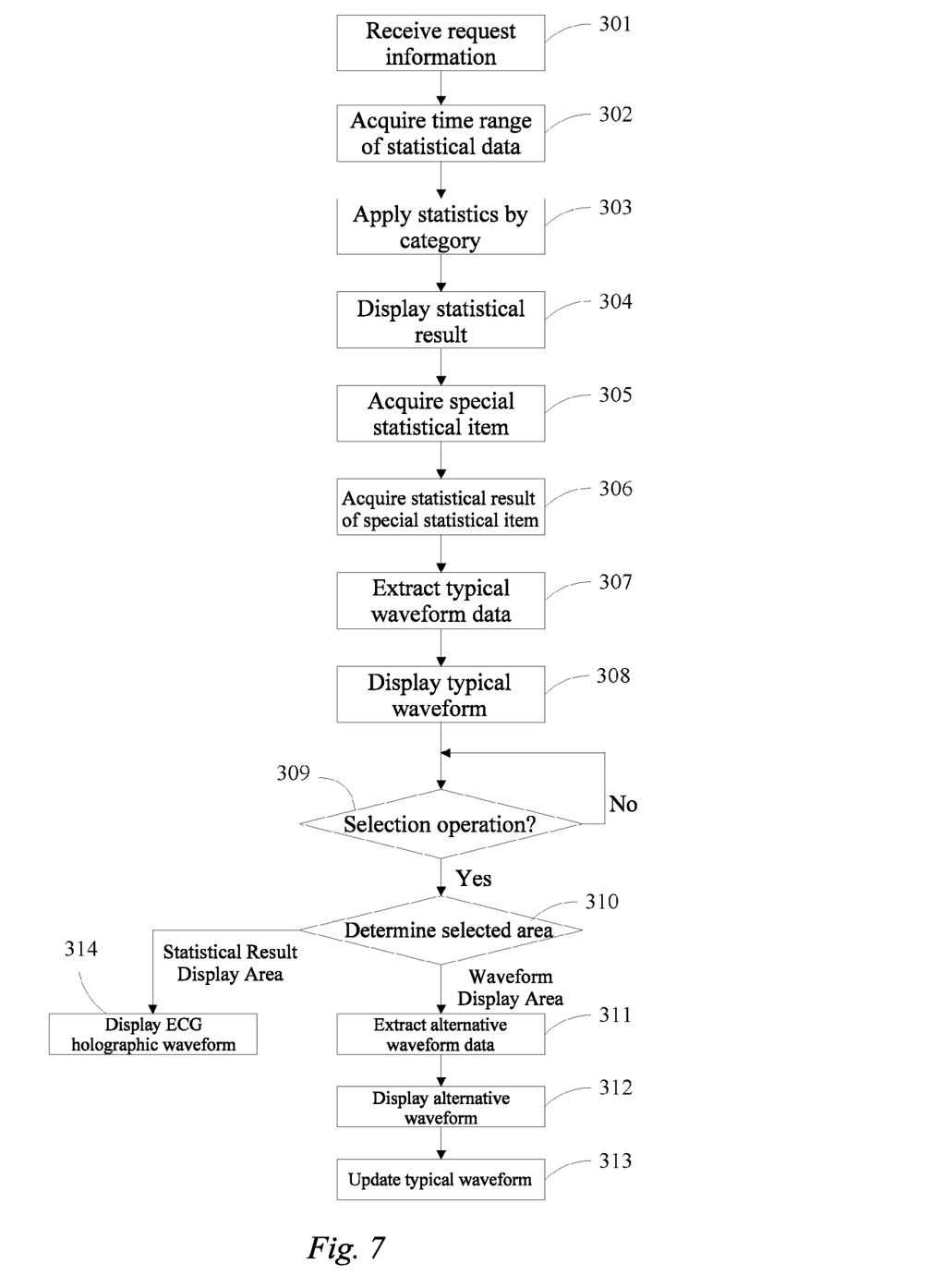
FIG. 7 is a flow chart of vital sign data statistics.

The vital-sign data statistics system can be implemented either by hardware, for example, by building an application specific integrated circuit through gate circuits, or by a program stored in a computer-readable medium and executed by a microprocessor. The flow of a vital-sign data statistics method is shown in FIG. 7, including the following steps.

In step 301, request information for requesting display of ECG data statistical results is received.

In step 302, a time range of statistical data is acquired based on the request information.

In step 303, statistics by category is applied to vital sign data within the time range according to set categories and statistical items of each of the categories.

In step 304, the statistical results of each category are displayed by category in a statistical result display area, which is at least a partial area of a display interface.

In step 305, a special statistical item set for each category is acquired.

In step 306, statistical results of the special statistical item are acquired from statistical contents of each category.

In step 307, typical waveform data are extracted. Waveform data including a predetermined period of time around the statistical results of the special statistical item are extracted from vital sign data within the time range, and the waveform data are taken as typical waveform data of the special statistical item.

In step 308, a typical waveform is displayed. The typical waveform data of all the special statistical items are respectively displayed in a waveform display area which is at least a partial area of the display interface.

In step 309, a selection operation of a user in the display interface is detected.

In step 310, when the selection operation of the user is detected, an area selected by the user is determined according to position coordinates of the selection operation. When the selected area is a waveform display area, step 311 is executed, and when the selected area is a statistical result display area, step 314 is executed.

In step 311, alternative waveform data are extracted. According to the position coordinates of the selection operation, the special statistical item corresponding to the area selected by the user is determined, at least one group of waveform data including a predetermined period of time around the relevant data are extracted, and the at least one group of waveform data are taken as alternative waveform data of the special statistical item.

In step 312, an alternative waveform is displayed. The typical waveform data and the alternative waveform data of the special statistical item are all taken as options to be displayed in rows in a pop-up selection window and the user is allowed to select between the typical waveform data and the alternative waveform data.

In step 313, after receiving a selection of the user, the typical waveform data displayed in the waveform display area of the special statistical item are updated.

In step 314, an ECG holographic waveform is displayed. According to the position coordinates of the selection operation, the statistical item selected by the user is determined, a holographic waveform display window of the vital sign data is popped up based on the selection operation, and the typical waveform of the special statistical item selected by the user is displayed in the current window of the holographic waveform display window.

It will be understood by those skilled in the art that all or some of the steps of the various methods in the embodiments described above could be achieved by relevant hardware commanded by a program, which program can be stored in a computer-readable storage medium. The storage medium may include read-only memory, random memory, magnetic disk or optical disk, etc. The data processing module can implement the above functions by executing the program.

The present disclosure has been described in detail with reference to specific examples, which are merely for the purpose of facilitating understanding of the present disclosure and are not intended to limit the present disclosure. It will be apparent to those skilled in the art that changes may be made to the specific embodiments described above in accordance with the teachings of the present disclosure.

What is claimed is:

1. A system for patient monitoring comprising:
   a signal collection module for collecting vital sign signals from a body of a patient;
   a data processing module connected to the signal collection module and configured for processing the vital sign signals and generating physiological parameters for reflecting a condition of the patient;
   a display module connected to the data processing module and configured for displaying a standard physiological parameters window comprising current monitored values for the physiological parameters and one or more respective waveforms including the current monitored values; and
   a vital-sign data statistics system, comprising:
      a request receiving unit for receiving request information for requesting display of statistical results of vital sign data obtained from the vital sign signals, the vital sign data including the current monitored values for the physiological parameters;
      a first acquisition unit for acquiring a time range of statistical data based on the request information;
      a statistical unit for applying statistics by category to the vital sign data within the time range according to set categories and statistical items of each of the set categories;
      a second acquisition unit, for acquiring a special statistical item set for each category;
      a third acquisition unit, for acquiring statistical results of the special statistical item from statistical contents of each category; and
      a fourth acquisition unit for extracting waveform data comprising a predetermined period of time around the occurrence of the statistical results of the special statistical item from the vital sign data within the time range, and taking the waveform data as typical waveform data of the special statistical item;
   wherein the display module is configured to cover at least a portion of the standard physiological parameters window including the current monitored values with a statistical results display area including visual data representing statistical results of each category, the display module being further configured to process the typical waveform data of all special statistical items into the visual data and respectively display the visual data in a statistical item waveform display area simultaneously with the statistical results display area.

2. The system of claim 1, wherein the vital-sign data statistics system further comprises a first positioning unit and an updating unit, and
   the first positioning unit being configured to capture a selection operation of a user in the statistical item waveform display area and determine the special statistical item corresponding to an area selected according to position coordinates of the selection operation;
   the fourth acquisition unit being configured to retrieve at least one relevant datum related to the special statistical item from the vital sign data within the time range, extract at least one group of waveform data comprising a predetermined period of time around the at least one relevant datum, and take the at least one group of waveform data as alternative waveform data of the special statistical item;
   the display module being further configured to process the typical waveform data and the alternative waveform data of the special statistical item into the visual data, display the visual data in rows in a pop-up selection window and allow the user to select between the typical waveform data and the alternative waveform data; and
   the updating unit being configured to update the typical waveform data of the special statistical item after receiving a selection of the user.

3. The system of claim 1, wherein the statistical results display area and the statistical item waveform display area are vertically or horizontally arranged side by side.

4. The system of claim 1, further comprising:
   means for capturing a selection operation of a user in the statistical results display area and determining the special statistical item selected by the user according to position coordinates of the selection operation; and
   the display module being further configured to pop up a holographic waveform display window of the vital sign data based on the selection operation and display in a current window of the holographic waveform display window the one or more respective waveforms at the time of occurrence of or the typical waveform data of the special statistical item selected by the user.

5. The system of claim 1, wherein the vital sign data are electroencephalography (ECG) data.

6. The system of claim 5, wherein the statistics by category of the ECG data comprise statistics of at least one of heart rate, ST, QT/QTc and arrhythmia events.

7. The system of claim 1, wherein the request information for requesting display of the statistical results of the vital sign data is generated based on a selection operation of a user on a display interface or based on switching of a state of an input unit provided on a patient monitor.

8. The system of claim 1, wherein:
at least one statistical category comprises a heart rate;
the statistical results display area includes at least one statistical item for heart rate selected from the group consisting of a fastest heart rate and a slowest heart rate; and
the statistical item waveform display area includes a heart rate waveform including a point in time at which the fastest or slowest heart rate was recorded as well as a period of time before and after the point in time at which the fastest or slowest heart rate was recorded.

9. The system of claim 8, wherein at least one of the statistical results display area and the statistical item waveform display area displays an occurrence time of the fastest heart rate or slowest heart rate.

10. The system of claim 1, wherein the display module is configured to entirely cover the standard physiological parameter window with one or both of the statistical results display area and the statistical item waveform display area.

11. The system of claim 1, wherein each category and statistical item is defined in a stored category table.

12. The system of claim 1, wherein the statistical results display area is presented in a pop-up window that is closable by a user to resume display of the standard physiological parameters window.

13. The system of claim 1, wherein the statistical results display area is automatically closed by the display module after a set time period without an operation being detected to resume display of the standard physiological parameters window.

14. A method for patient monitoring comprising:
collecting vital sign signals from a body of a patient;
processing the vital sign signals and generating physiological parameters for reflecting a condition of the patient;
displaying a standard physiological parameters window comprising current monitored values for the physiological parameters and one or more respective waveforms including the current monitored values;
receiving a request for display of statistical results of vital sign data obtained from the vital sign signals, the vital sign data including the current monitored values for the physiological parameters;
acquiring a time range of statistical data based on the request;
applying statistics by category to the vital sign data within the time range according to set categories and statistical items of each of the set categories;
acquiring a special statistical item set for each category;
acquiring statistical results of the special statistical item from statistical contents of each category;
extracting waveform data comprising a predetermined period of time around the occurrence of the statistical results of the special statistical item from the vital sign data within the time range, and taking the waveform data as typical waveform data of the special statistical item;
replacing at least a portion of the standard physiological parameter window including the current monitored values with a statistical results display area including visual data representing statistical results of each category, such that at least a portion of the standard physiological parameters window is covered including the current monitored values with the statistical results display area including visual data representing statistical results of each category; and
processing the typical waveform data of all special statistical items into the visual data and respectively display the visual data in a statistical item waveform display area simultaneously with the statistical results display area.

* * * * *